United States Patent [19]

Ford

[11] Patent Number: 5,885,629

[45] Date of Patent: *Mar. 23, 1999

[54] STABLE, OPTICALLY CLEAR COMPOSITIONS

[75] Inventor: Michael Anthony Ford, Coleford, United Kingdom

[73] Assignee: SmithKline Beecham p.l.c., Brentford, United Kingdom

[ * ] Notice: The term of this patent shall not extend beyond the expiration date of Pat. No. 5,607,707.

[21] Appl. No.: 716,254

[22] PCT Filed: Mar. 9, 1995

[86] PCT No.: PCT/EP95/00899

§ 371 Date: Sep. 13, 1996

§ 102(e) Date: Sep. 13, 1996

[87] PCT Pub. No.: WO95/24832

PCT Pub. Date: Sep. 21, 1995

[30] Foreign Application Priority Data

Mar. 15, 1994 [GB] United Kingdom .................. 9405041

[51] Int. Cl.⁶ ...................................... A23L 1/275
[52] U.S. Cl. .............................. 426/2; 426/602; 426/262; 426/604; 426/540; 426/541; 426/73; 424/439
[58] Field of Search ................................ 426/2, 602, 262, 426/604, 540, 541, 73; 424/439

[56] References Cited

U.S. PATENT DOCUMENTS

| | | |
|---|---|---|
| 3,886,294 | 5/1975 | Emodi et al. . |
| 3,998,753 | 12/1976 | Antoshkiw et al. . |
| 4,835,002 | 5/1989 | Wolf et al. . |
| 5,023,095 | 6/1991 | Kirk . |
| 5,607,707 | 3/1997 | Ford .................................... 426/602 |

FOREIGN PATENT DOCUMENTS

| | | |
|---|---|---|
| 571 677 | 12/1993 | European Pat. Off. . |
| 2 187 291 | 1/1974 | France . |
| 40 20 874 | 1/1991 | Germany . |
| WO94-06310 | 3/1994 | WIPO . |

OTHER PUBLICATIONS

Lundberg et al., *Chemistry and Physics of Lipids,* vol. 14 (1975) pp. 260–262.

*Encyclopedia of Chemical Technology,* 1979, pp. 900–930.

*Primary Examiner*—Carolyn Paden
*Attorney, Agent, or Firm*—Dara L. Dinner; Stephen Venetianer

[57] ABSTRACT

Stable aqueous compositions of biologically active oils for the preparation of optically clear products for use in human or animal healthcare, for example beverages, are prepared by a process comprising: (a) mixing 0.001–2.0% w/w of a biologically active oil or 0.1–2.0% w/w of a biologically active oil as a 20–30% dispersion in a suitable oil with 0.1–1.0% of an antioxidant or antioxidant mixture, (b) dispersing the mixture from (a) in 2–20 % of an emulsifier or an emulsifier mixture having an HLB (hydrophilc-lipophilic balance) value of 10 to 18 and heating to 50° to 150° C. so as to yield a transparent mixture, (c) raising the temperature of the mixture from (b) as appropriate whilst maintaining stirring to maintain a transparent mixture, and (d) combining the mixture from (c) with water having a minimum temperature of 95° C. while continuously stirring to provide a trasparent composition.

25 Claims, No Drawings

STABLE, OPTICALLY CLEAR COMPOSITIONS

FIELD OF THE INVENTION

The present invention relates to compositions for products for internal or external use by humans or animals, such as beverages, processes for preparing such compositions and products containing them. In particular the invention relates to a process for preparing liquid compositions comprising biologically active oils for use in the maintenance and/or promotion of health.

SUMMARY OF THE INVENTION

The present invention therefore in one aspect provides an aqueous composition for the preparation of optically clear products for human or animal healthcare comprising 0.001 to 2.0% w/w of a biologically active oil or 0.1–2.0% w/w of a biologically active oil as a 20–30% dispersion in a suitable oil, 2–20% of an emulsifier having an HLB (hydrophilic/lipophilic balance) value of from 10 to 18 or where a blend of emulsifiers is employed, a calculated HLB value of from 10 to 18, and 0.1 to 1.0% of an antioxidant or a mixture of antioxidants.

DETAILED DESCRIPTION OF THE INVENTION

Another aspect of the present invention are stable aqueous compositions of biologically active oils for the preparation of optically clear products for use in human or animal healthcare, for example beverages, are prepared by a process comprising: (a) mixing 0.001–2.0% w/w of a biologically active oil or 0.1–2.0% w/w or a biologically active oil as a 20–30% dispersion in a suitable oil with 0.1 1.0% of an antioxidant or antioxidant mixture, (b) dispersing the mixture for (a) in 2–20% of an emulsifier or an emulsifier mixture having an HLB (hydrolipophilic balance) value of 10 to 18 and heating to 50° to 150° C. so as to yield a transparent mixture, (c) raising the temperature of the mixture from (b) as appropriate while maintaining stirring to maintain a transparent mixture, and (d) combining the mixture from (c) with water having a minimum temperature of 95° C. while continuously stirring to provide a transparent composition.

An example of a blend of emulsifiers is a blend containing 4 parts of Span 20 (sorbitan monolaurate) and 6 parts of Tween 60 (polyoxyethylene sorbitan monostearate) having an effective HLB value of $0.4 \times 8.6 + 0.6 \times 14.9 = 12.3$.

By 'optically clear' we mean a product exhibiting a percentage transmittance value of not less than about 95%, preferably 98%, determined at a wavelength of 800 nm in a 1 cm path length cuvette.

By a 'biologically active oil' we mean natural or synthetic oils which are or contain biologically active agents in particular prophylactic or therapeutic agents.

Surprisingly it has been found that the composition of the present invention is able to yield a product with desirable properties, particularly high water solubility using ingredients which have hitherto been found to be difficult to solubilise satisfactorily in this kind of product.

Preferably the biologically active oil is an oil of natural origin for example from the seeds or flowers of the Ribes, Boraginaceae, Labitae, Onagraceae and Curcubitaceae species, oils of fungal origin, fish oils or other natural oils. Preferred oils include evening primrose oil, borage/starflower oil and blackcurrant seed oil.

Suitably the amount of oil is 0.001–2.0% preferably 0.1–1.0% by weight expressed as the pure substance. Oils for use in the present invention can be extracted from natural sources by processes known in the art. The oils are commercially available, for example, from Sigma Chemical Co., Poole, Dorset.

The compositions may contain more than one biologically active oil.

Other biologically active ingredients can be used in the composition according to the invention, in particular carotenoid pigments eg. β-carotene to produce a useful combination of colour and nutritional biochemicals.

The biologically active oils may be mixed or dispersed with other suitable oils in particular, consumable oils for example, corn, peanut, safflower, olive and rapeseed oils as well as many essential oils particularly those used in beverages used to give flavours, such as citrus oils.

The emulsifier may be any anionic, cationic, amphoteric or non-ionic emulsifier or mixture of emulsifiers which is suitable for consumption by or application to the human or animal body. Preferably the emulsifier is a non-ionic emulsifier or a mixture and preferably having an HLB (hydrophilic/lipophilic balance) of 12–16 and most preferably has an HLB value of 15. Preferred compounds include Tween 60 (polyoxyethylene(20)sorbitan monostearate and Tween 40 (polyoxyethylene(20)sorbitan monopalmitate) available from ICI Speciality Chemicals, Leatherhead, Surrey.

Suitably the emulsifier is a binary or tertiary blend of emulsifiers, for example blends of Tween 60 with a sucrose ester emulsifier (manufactured by Mitsubishi Kasei Food Corporation, Ichikawa Building, 13-3 Ginza 5-Chome, Chuo-ku, Tokyo 104, Japan) or blends of Tween 60 and sucrose ester and a polyglycerol ester of a fatty acid (available from Grindsted Products Limited., Northern Way, Bury St. Edmunds, Suffolk).

The amount of emulsifier in the composition is selected as an amount which will vary depending upon which specific biologically active oil is used, its method of preparation, and how much is included. For example an oil-based dispersion containing 1% by weight of biologically active oil will generally require emulsifier(s) in the range of 2–8-% w/w to achieve a clear dispersion and so as not to have significant adverse flavour effects in typical drinks when diluted.

Preferably the emulsifier is a polysorbate, in particular polysorbate 60 in the case of consumable products as it has the advantage of having the least noticeable taste. Therefore, a particularly useful feature of the present invention is the ability to produce a flavourless composition. In a particularly preferred composition the biologically active oils are blackcurrant seed oil and α-tocopherol and the emulsifier is a polysorbate.

The antioxidant used in the present invention can be for example, alpha-tocopherol, tocopheryl acetate, ascorbic acid, ascorbyl palimitate, butylated hydroxyanisole (BHA) and butylated hydroxytoluene (BHT) or a mixture of such antioxidants. Particularly preferred antioxidants are α-tocopherol, tocopheryl acetate, ascorbyl palmitate and ascorbic acid.

An important advantage of the compositions of the present invention over known compositions is one of economy since it avoids the use of large amounts of added lipids and emulsifiers. The compositions offer the opportunity of presenting these materials in the form of an attractive, palatable beverage. They can be used to give a wider range of products, particularly reduced fat products with new and interesting flavour possibilities.

Whilst the present invention is particularly useful in the production of optically clear products, the present invention can also be used to prepare opaque, cloudy products. A frequent problem with such products, particularly those products containing emulsified oils is that of 'neck ringing'. The compositions prepared according to the present invention have been found not to exhibit this problem. It will be appreciated that the compositions of the present invention may be used for products in the pharmaceutical or veterinary field other than beverages, such as vitamin and cough syrups, throat sprays, lotions and mouthwashes, particularly where optical clarity is important.

Certain biologically active oils contain vitamins and provitamins such as vitamins A,D, E, carotenoid pigments and nutritionally important fatty acids.

In the compositions of the present invention the biologically active oils are believed to be finely dispersed in a micellar form or as microemulsions because they exhibit certain characteristics eg. transparency when viewed by transmitted light.

Therefore a further advantage of the compositions according to the present invention is that the fine dispersion of these oils in aqueous preparations will help to promote their efficient uptake by body tissues when the composition is presented to the body. Whilst the small particle size of the particles of biologically active oils favour their uptake, the simultaneous presentation or ingestion of the oils with an emulsifier will also encourage efficient transfer of these substances across membranes.

The formulations according to the invention also have surprising acid resistance. This is advantageous because prior to absorption from the intestinal tract, the preparation is able to survive the strongly acid conditions of the stomach.

In a further aspect of the invention there is provided a method of administration of an oil-soluble material to a human or animal body by treating said body with a composition according to the invention. Preferably the composition is administered orally, for example in the form of a liquid composition.

The composition obtained according to the present invention is an aqueous dispersion which is capable of dissolution in water-based products to yield optically clear finished products. It will be appreciated that further ingredients may optionally be included in the composition of the present invention or to the final food product, for example sweeteners, preservatives (eg. sulphur dioxide, benzoic acid and sorbic acid), proteins, fats, vitamins, minerals and other materials employed in the preparation of food and drink products. Optionally the compositions also contain antioxidant cofactors such as zinc, selenium and manganese which are needed for the body's naturally occurring antioxidant enzymes. Preferably the final product is flavoured; this can be achieved by the addition of naturally flavoured foods such as fruit juices and concentrates, extracts and compounds or flavouring additives. Preferably further nutritive ingredients are added to the final drink such as other vitamins and minerals as described in "The Food Labelling Regulations 1984" Statutory Instrument No. 1305 (1984) H.M.S.O., London.

Suitably processing aids can be incorporated. Such aids may include ingredients which influence pH, redox potential, enzyme activity, hydrogen bonding and/or other aspects. Processing aids are for example sulphur dioxide, other antioxidants, metal salts, acids (eg. phosphoric and citric acid), alkalis, surfactants such as lecithin and starch plasticisers eg. calcium chloride. Preferred processing aids for inclusion are anti-foaming agents eg. silicones.

Ingredients subject to a loss of nutritional value are added at a late stage of the process. Optionally the product can be produced in light or oxygen excluding containers after preparation to increase protection of materials sensitive to light or oxygen induced degradation. Optionally the product can be carbonated.

A further aspect of the invention provides a process for the preparation of an aqueous composition for the preparation of optically clear products for use in human or animal healthcare which process comprises:

a) mixing a biologically active oil with an antioxidant/ antioxidant mixture b) dispersing the oil-antioxidant mixture in the emulsifier while heating to between 50°–150° C. so as to yield a transparent mixture c) raising the temperature of the mixture as appropriate whilst maintaining stirring to maintain a transparent mixture, and d) combining the mixture with water having a minimum temperature of 95° C. while continuously stirring to provide a transparent composition.

Optionally the antioxidant in a) is dispersed initially with the emulsifier before mixing with the biologically active oil. Preferably in d) the mixture and the water are combined by adding the mixture to the water.

One advantage of the present invention is the wide range of temperatures which can be used in b) above. The lower temperatures are particularly useful where more temperature sensitive ingredients are involved. The higher temperatures are useful in that significantly less emulsifier(s) is needed. The use of these high temperatures incurs the risk of degradation of the oil unless suitable precautions are taken. For example it is necessary to incorporate an antioxidant in the initial stages of preparation and it is desirable to exclude oxygen by heating the mixture in an atmosphere of nitrogen.

In the preparation of the composition according to d) above it is important that the mixture is combined with the water gradually so as to maintain transparency and for best or most consistent results the mixture is added to the water.

In a preferred process the biologically active oil(s) and antioxidant (s) are dissolved in polysorbate emulsifier. In another preferred process according to the present invention a biologically active oil is added to a polysorbate emulsifier/ antioxidant mixture.

In a further aspect of the present invention additional water is added to the composition to yield an aqueous intermediate product which is suitable for use in a suitable water-based product.

The invention is illustrated by the following Examples.

EXAMPLE 1

Blackcurrant seed oil Composition

|  | % w/w |
| --- | --- |
| Blackcurrant seed oil | 1.0 |
| antioxidant (α-tocopherol) | 0.3 |
| emulsifier (Polysorbate 40 or 60) | 5.0 |
| water to | 100 |

The above components are combined as follows. The oil and antioxidant(s) are mixed at a temperature not exceeding 40° C. The emulsifier is added and the temperature of the mixture raised to at least 80° C. while maintaining stirring. At this point the mixture should be transparent. The mixture is added slowly at a rate of 50 ml per minute to about 75% of the final volume of hot water having a minimum temperature of 95° C. while maintaining stirring. The diluted mixture is cooled to room temperature and diluted with water to the final volume. As an alternative after adding the emulsifier and heating as given above the hot water is added slowly to the oil-antioxidant mixture at the rate of 50 ml per minute while stirring. When half the volume of water has been added there is a noticeable increase in viscosity. Continuing to add the water to the required volume reduces the viscosity and yields a clear, colourless or faintly coloured composition.

EXAMPLE 2

Blackcurrant Seed Oil and Colour Composition

|  | % w/w |
| --- | --- |
| β-carotene (30% dispersion) | 0.33 |
| Blackcurrant seed oil | 1.2 |
| antioxidant (α-tocopherol) | 0.3 |
| emulsifier (Polysorbate 40 or 60) | 9 |
| water to | 100 |

The antioxidant is dispersed in the emulsifier while heating to approximately 40° C. The blackcurrant seed oil is added and stirred to yield a transparent mixture. The β-carotene is then added while continuing to stir and the temperature of the mixture raised to 140° C. At this point the mixture should remain transparent. Finally, the mixture is added to hot water as detailed in Example 1 above.

EXAMPLE 3

Blackcurrant seed oil Composition

|  | % w/w |
| --- | --- |
| Blackcurrant seed oil | 0.3 |
| antioxidant (α-tocopherol) | 0.3 |
| emulsifier 1 (Polysorbate 60) | 6.0 |
| emulsifier 2 (sugar ester S-1170) | 0.25 |
| emulsifier 3 (Triodan) | 0.25 |
| water to | 100 |

The antioxidant is dispersed in emulsifier 1 while heating to approximately 40° C. Emulsifiers 2 and 3 are added and the temperature raised to 120° C. The blackcurrant seed oil is added while maintaining stirring; at this point the mixture should be transparent. Finally, the mixture is added to hot water as detailed in Example 2.

EXAMPLE 4

Blackcurrant seed oil Composition

|  | % w/w |
| --- | --- |
| Blackcurrant seed oil | 0.5 |
| antioxidant (α-tocopherol) | 0.1 |
| emulsifier 1 (Polysorbate 60) | 3.0 |
| emulsifier 2 (Triodan)* | 0.5 |
| *Grinstead Products Ltd. water to | 100 |

*Grinstead Products Ltd.

The antioxidant is dispersed in emulsifier 1 while heating to approximately 40° C. Emulsifier 2 is added and the temperature raised to 120° C. The blackcurrant seed oil is added while maintaining stirring; at this point the mixture should be transparent. Finally, the mixture is added to hot water as detailed in Example 2.

EXAMPLE 5

Formulations

| 5.1 Carbonated, clear blackcurrant flavoured drink | |
| --- | --- |
|  | % w/v |
| Sucrose | 10.0 |
| Citric acid | 0.25 |
| Sodium benzoate | 0.017 |
| Ascorbic acid | 0.030 |
| Flavouring as required |  |
| Blackcurrant seed oil composition (Example 1) | 0.5 (% v/v) |
| Water | to 100 vol |
| Carbon dioxide to 2.5 volumes |  |

Using an oil composition of the type detailed in example 1, experimental products have been prepared containing the oil in concentrations ranging from 20 to 1000 mg per liter. All were characterised by possessing optical clarity without any evidence of 'neck ringing'.

Typical opaque drink products in which the colour compositions can be employed are (examples 5.2 and 5.3):

|  | % w/v |
| --- | --- |
| 5.2 Carbonated fruit crush drink | |
| Orange juice | 5.2 |
| Sucrose | 7.5 |
| Citric acid | 0.3 |
| Sodium benzoate | 0.007 |
| Ascorbicacid | 0.040 |
| Blackcurrant seed oil and colour composition (Example 2) | 1.0 (% v/v) |
| Flavouring as required |  |
| Water | to 100 vol |
| Carbon dioxide to 2.5 volumes | |
| 5.3 Blackcurrant flavour milk drink | |
| Skimmed milk | 51.0 |
| Carbohydrate | 9.4 |
| Citric acid | 0.9 |
| Sodium carboxymethylcellulose | 0.94 |
| Ascorbic acid | 0.030 |
| Colour composition 3 | 1.0 (% v/v) |
| Flavourings as required |  |
| Water | to 100 vol |
| 5.4 Antioxidant vitamin syrup | |
| Tocopherol acetate | 0.633 |
| Ascorbic acid | 1.333 |
| Glucose syrup | 85.0 |
| Propylene glycol | 1.0 |
| Sodium citrate | 0.024 |

-continued

|  | % w/v |
|---|---|
| Citric acid | 0.25 |
| Sodium benzoate | 0.1 |
| Flavourings as required |  |
| Blackcurrant seed oil composition (Example 1) | 10.0 (% v/v) |
| Water | to 100 vol |

I claim:

1. An optically clear aqueous composition comprising 0.001 to 2.0% w/w of a biologically active oil, 2 to 20% of an emulsifier or a mixture of emulsifiers, having an HLB (hydrolipophilic balance) value of from 10 to 18, 0.1 to 1.0% of an antioxidant or a mixture of antioxidants, and water.

2. A composition as claimed in claim 1 which further comprises a colouring ingredient.

3. A composition as claimed in claim 1 wherein the amount of biologically active oil is 0.1–1.0%.

4. A composition as claimed in claim 3 wherein the biologically active oil is selected from the group consisting of an oil from the seed or flower of the Ribes, Boraginaceae, Labitae, Onagracae, or Curcubitaceae species; or mixture thereof.

5. The composition as claimed in claim 4 wherein the oil is evening primrose oil, borage or starflower oil, or blackcurrent seed oil.

6. A composition as claimed in claim 3 wherein the biologically active oil is an oil of fungal origin, or a fish oil.

7. A composition as claimed in claim 1 wherein the amount of emulsifier is from 8 to 10%.

8. A composition as claimed in claim 1 wherein the amount of antioxidant is 0.3 to 0.5%.

9. A composition as claimed in claim 1 further comprising ascorbic acid or alpha tocopherol, or mixtures thereof.

10. A beverage comprising the composition according to claim 1.

11. A process for the preparation of an optically clear aqueous composition comprising 0.001 to 2.0% w/w of a biologically active oil, 2 to 20% of an emulsifier or a mixture of emulsifiers, having an HLB (hydrolipophilic balance) value of from 10 to 18, 0.1 to 1.0% of an antioxidant or a mixture of antioxidants, and water which process comprises:
 a) mixing the biologically active oil with an antioxidant or an antioxidant mixture,
 b) dispersing the oil-antioxidant mixture of step (a) in the emulsifier while heating to between 50°–150° C. so as to yield a transparent mixture,
 c) raising the temperature of the transparent mixture of step (b) as appropriate while maintaining stirring to maintain the transparency of the mixture, and
 d) combining the transparent mixture of step (c), with water having a minimum temperature of 95° C. while continuously stirring to provide a transparent composition.

12. The product of the process of claim 11.

13. A method of administering an oil-soluble material to a human or animal in need thereof, which method comprises administering to said human or animal an optically clear aqueous composition comprising 0.001 to 2.0% w/w of a biologically active oil, 2 to 20% of an emulsifier or a mixture of emulsifiers, having an HLB (hydrolipophilic balance) value of from 10 to 18, 0.1 to 1.0% of an antioxidant or a mixture of antioxidants, and water.

14. An optically clear aqueous composition comprising
 a) 0.001 to 2.0% w/w of a biologically active oil which is selected from the group consisting of an oil from the seed or flower of the Ribes, Boraginaceae, Labitae, Onagracae, or Curcubitaceae species; or mixtures thereof;
 b) 2 to 20% of an emulsifier or a mixture of emulsifiers, having an HLB (hydrolipophilic balance) value of from 10 to 18;
 c) 0.1 to 1.0% of an antioxidant or a mixture of antioxidants; and
 d) water.

15. The composition according to claim 14 wherein the biologically active oil is present in an amount of 0.1 to 2.0% w/w in a 20 to 30% dispersion of a consumable oil.

16. The composition according to claim 15 wherein the emulsifier is in the range of 2 to 8% w/w and is
 a) polysorbate or a blend of polysorbates; or
 b) polysorbate or a blend of polysorbates with a sucrose ester emulsifier; or
 c) polysorbate or a blend of polysorbates, a sucrose ester and a polyglycerol ester of a fatty acid.

17. The composition according to claim 15 wherein the consumable oil is selected from the group consisting of corn, peanut, safflower, olive, rapeseed, or citrus oil.

18. The composition according to claim 14, wherein the emulsifier is
 a) polysorbate or a blend of polysorbates; or
 b) polysorbate or a blend of polysorbates with a sucrose ester emulsifier; or
 c) polysorbate or a blend of polysorbates, a sucrose ester and a polyglycerol ester of a fatty acid.

19. The composition according to claim 14 which comprises ascorbic acid or alpha-tocopherol, or mixtures thereof.

20. An optically clear aqueous composition comprising
 a) a biologically active oil which is selected from the group consisting of an oil from the seed or flower of the Ribes, Boraginaceae, Labitae, Onagracae, or Curcubitaceae species, or mixtures thereof; which active oil is present in the amount of 0.1 to 2.0% w/w as a 20 to 30% w/w dispersion in a consumable oil which oil is selected from the group consisting of corn, peanut, safflower, olive, rapeseed, or citrus oil;
 b) 2 to 20% of an emulsifier which is
  (i) a polysorbate or a blend of polysorbates; or
  (ii) a polysorbate or a blend of polysorbates with a sucrose ester emulsifier; or
  (iii) a polysorbate or a blend of polysorbates, a sucrose ester and a polyglycerol ester of a fatty acid; said emulsifier having an HLB (hydrolipophilic balance) value of from 10 to 18;
 c) 0.1 to 1.0% of an antioxidant or a mixture of antioxidants; and
 d) water.

21. The composition as claimed in claim 20 wherein the oil is evening primrose oil, borage or starflower oil, or blackcurrent seed oil.

22. An optically clear aqueous composition comprising
 a) 0.001 to 2.0% w/w of a biologically active oil selected from the group consisting of an oil from the seed or flower of the Ribes, Boraginaceae, Labitae, Onagracae, or Curcubitaceae species; or mixtures thereof;
 b) 2 to 20% of an emulsifier which is
  (i) a polysorbate or a blend of polysorbates; or
  (ii) a polysorbate or a blend of polysorbates with a sucrose ester emulsifier; or
  (iii) a polysorbate or a blend of polysorbates, a sucrose ester and a polyglycerol ester of a fatty acid; said emulsifier having an HLB (hydrolipophilic balance) value of from 10 to 18;

c) 0.1 to 1.0% of an antioxidant or a mixture of antioxidants; and d) water.

23. The composition according to claim 22 which further comprises β-carotene.

24. A method of administering an oil-soluble material to an human or animal in need thereof, which method comprises administering to said human or animal an optically clear aqueous composition comprising a) 0.001 to 2.0% w/w of a biologically active oil selected from the group consisting of an oil from the seed or flower of the Ribes, Boraginaceae, Labitae, Onagracae, or Curcubitaceae species; or mixtures thereof;

b) 2 to 20% of an emulsifier which is
  (i) a polysorbate or a blend of polysorbates; or
  (ii) a polysorbate or a blend of polysorbates with a sucrose ester emulsifier; or
  (iii) a polysorbate or a blend of polysorbates, a sucrose ester and a polyglycerol ester of a fatty acid; said emulsifier having an HLB (hydrolipophilic balance) value of from 10 to 18;

c) 0.1 to 1.0% of an antioxidant or a mixture of antioxidants; and d) water.

25. A process for the preparation of an optically clear aqueous composition comprising 0.001 to 2.0% w/w of a biologically active oil, 2 to 20% of an emulsifier or a mixture of emulsifiers, having an HLB (hydrolipophilic balance) value of from 10 to 18, 0.1 to 1.0% of an antioxidant or a mixture of antioxidants, and water which process comprises:

a) dispersing the antioxidant or an antioxidant mixture in the emulsifier, prior to mixing with the biologically active oil;

b) heating the mixture of step (a) to between 50°–150° C. so as to yield a transparent mixture;

c) raising the temperature of the transparent mixture of step (b) as appropriate while maintaining stirring to maintain the transparency of the mixture, and d) combining the transparent mixture of step (c), with water having a minimum temperature of 95° C. while continuously stirring to provide a transparent composition.

* * * * *